United States Patent [19]

Schoen et al.

[11] Patent Number: 4,550,112

[45] Date of Patent: Oct. 29, 1985

[54] 3,7-DIAZABICYCLO(3,3,1)NONANE COMPOUNDS AND THEIR USE IN TREATING HEART DISEASE

[75] Inventors: Uwe Schoen, Hanover; Bernd Hachmeister, Isernhagen; Wolfgang Kehrbach, Hanover; Ulrich Kuehl, Gehrden; Gerd Buschmann, Hanover, all of Fed. Rep. of Germany

[73] Assignee: Kali-Chemie Pharma GmbH, Hanover, Fed. Rep. of Germany

[21] Appl. No.: 532,762

[22] Filed: Sep. 16, 1983

[30] Foreign Application Priority Data

Sep. 18, 1982 [DE] Fed. Rep. of Germany ....... 3234697

[51] Int. Cl.$^4$ ................. A61K 31/445; C07D 471/08; C07D 471/10
[52] U.S. Cl. ..................................... 514/278; 514/300; 546/18; 546/122
[58] Field of Search .................. 546/122, 18; 424/256; 514/278, 300

[56] References Cited

U.S. PATENT DOCUMENTS 3,962,449  6/1976  Binnig et al. .................... 424/267

FOREIGN PATENT DOCUMENTS 2428792  1/1976  Fed. Rep. of Germany .......... 471/8
2749584  5/1978  Fed. Rep. of Germany ........ 221/22
2658558  6/1978  Fed. Rep. of Germany ...... 546/122

OTHER PUBLICATIONS

Welner et al., Israel J. of Chemistry, vol. 4 (1966) pp. 39-45.
Eur. J. Med. Chem., 1977, pp. 301-305.
Chem. Ber., vol. 110, p. 3894.
J. Chem. Soc., vol. 115, p. 686 (1919).
Israel J. Chem., vol. 4, p. 39 (1966).
Austral. J. Chem., vol. 13, p. 129 (1960).

Basic Principles of Organic Chemistry—Roberts & Caserio, pp. 643 & 680 (1965).
Advanced Organic Chemistry—J. March (2d ed.) pp. 226-231 (Chapter 8).

Primary Examiner—Henry R. Jiles
Assistant Examiner—Bernard I. Dentz
Attorney, Agent, or Firm—Schwartz, Jeffery, Schwaab, Mack, Blumenthal & Evans

[57] ABSTRACT

Novel 3,7-diaza bicyclo-(3,3,1)-nonane compounds are described which are represented by the formula:

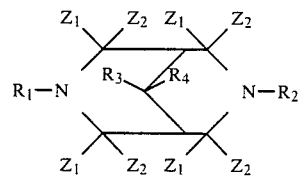

wherein
$Z_1$ and $Z_2$ each denotes hydrogen,
$R_1$ and $R_2$ each denotes (A) a substituent which contains up to 12 carbon atoms and which is selected from the group consisting of alkyl, alkenyl, and alkinyl, or (B) a cycloalkyl group containing 3 to 6 carbon atoms which is attached to the nitrogen atom directly or by an alkylene group containing 1 to 3 carbon atoms, and
$R_3$ and $R_4$ each denotes an alkyl group with up to 7 carbon atoms, or both together form an alkylene chain represented by the formula $-(CH_2)_n-$, wherein n is an integer ranging between about 3 and 6, such that the substituents $R_1$, $R_2$, $R_3$, and $R_4$ together contain at least 5 carbon atoms. Also described are processes of producing said compounds, pharmaceutical compositions containing compounds of Formula I, and methods of preparing and using said compositions.

24 Claims, No Drawings

3,7-DIAZABICYCLO(3,3,1)NONANE COMPOUNDS AND THEIR USE IN TREATING HEART DISEASE

BACKGROUND OF THE INVENTION

1. Field of the Invention

The present invention relates to novel and valuable diaza bicyclo-(3,3,1)-nonane compounds, to processes of producing such compounds, to pharmaceutical compositions containing diaza bicyclo-(3,3,1)-nonane compounds and their pharmaceutically acceptable acid addition salts, to processes of making such pharmaceutical compositions, and to methods of using said compositions in therapy.

2. The Prior Art 3,7-Diaza bicyclo-(3,3,1)-nonane compounds have become of considerable interest in chemical as well as in pharmacological respect. The chemistry of said compounds is described, for instance, in the following publications:

Russian, Chem. Rev. vol. 34, page 439 (1965);
Ann. Ist. Super Sanita, vol. 4, page 157 (1968);
J. Org. Chem. vol. 33, page 355 (1968)
Russian, Chem. Rev. vol. 42, page 190 (1973);
Chem. Ber. vol. 110, page 3894;
Austral. J. Chem. vol. 13, page 129 (1960);
J. Chem. Soc. vol. 115, page 686 (1919);

Pharmacological studies of said compounds have been described, for instance, in the following publication:
Eur. J. med. chem. 1977, pages 301–305.

The pharmacological properties of the known compounds extend from a relatively low local anesthetic activity as described in J. Chem. Soc. 1951, page 1706;

and an effect on the central nervous system as described in Published German Applications No. 26 58 558 and No. 27 49 584, up to a noteworthy antiarrhythmic activity as described in Published German Applications No. 24 28 792; No. 27 26 571, and No. 27 44 248.

SUMMARY OF THE INVENTION

It is one object of the present invention to provide novel and valuable diaza bicyclo-(3,3,1)-nonane compounds which are characterized by a pharmacological profile of activity differing from that of the known compounds of similar structure.

Another object of the present invention is to provide simple and effective processes of producing such novel diaza bicyclo-(3,3,1)-nonane compounds.

Another object of the present invention is to provide valuable intermediate products which can advantageously be used in preparing the novel and pharmacologically highly effective diaza bicyclo-(3,3,1)-nonane compounds.

A further object of the present invention is to provide novel and effective pharmaceutical compositions containing said novel diaza bicyclo-(3,3,1)-nonane compounds.

Still another object of the present invention is to provide a highly effective method of using such pharmaceutical compositions in therapy.

Other objects of the present invention and advantageous features thereof will become apparent as the description proceeds.

The present invention is directed to novel diaza bicyclo-(3,3,1)-nonane compounds of the following formula I

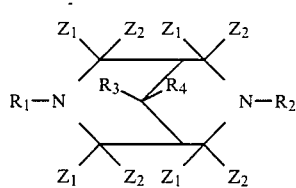

In formula I
$Z_1$ and $Z_2$ each denotes hydrogen, or both together form an oxygen while
$R_1$ and $R_2$ denote hydrogen, alkyl, alkenyl, or alkinyl, and
$R_3$ and $R_4$ each denote an alkyl group, or both together form an alkylene group.

However, the designation of the above given substituents is characterized and limited by the following provisos:

(1a) When both substituents $R_1$ and $R_2$ are hydrogen and $Z_1$ and $Z_2$ together form oxygen, then the substituents $R_3$ and $R_4$ are alkyl with at least 2 carbon atoms and not methyl, or $R_3$ and $R_4$ together form an alkylene group other than tetramethylene or pentamethylene, i.e., $R_3$ and $R_4$ together form an alkylene group with less than 4 or more than 5 carbon atoms in the alkylene group.

(1b) When both substituents $R_1$ and $R_2$ are hydrogen and $Z_1$ and $Z_2$ are also both hydrogen, then $R_3$ and $R_4$ are not both methyl, i.e., they are alkyl with at least 2 carbon atoms or one of them can be methyl and the other one alkyl with at least 2 carbom atoms.

(2) When only one of the substituents $R_1$ and $R_2$ is hydrogen and the other one is methyl or ethyl, then $R_3$ and $R_4$ cannot both be methyl, nor can they together form tetramethylene or pentamethylene, i.e., then at least one of $R_3$ and $R_4$ is alkyl with at least 2 carbon atoms or together they form alkylene with less than 4 or more than 5 carbon atoms.

(3) When both substituents $R_1$ and $R_2$ are not hydrogen but are alkyl, alkenyl, or alkinyl, then the substituents $R_1$, $R_2$, $R_3$ and $R_4$ together must contain at least 5 carbon atoms.

According to a preferred variant of the present invention each of the substituents $R_1$ and/or $R_2$ of the diaza bicyclo-(3,3,1)-nonane compound contains up to 12 carbon atoms and advantageously up to 7 carbon atoms.

As far as the substituents $R_1$ and $R_2$ indicate alkyl, such alkyl substituents can be branched alkyl groups as well as straight-chain alkyl groups. Straight-chain alkyl substituents are methyl, ethyl, n-propyl, n-butyl, n-pentyl, n-hexyl, or n-heptyl groups. Suitable branched alkyl substituents are iso-propyl, secondary butyl, (2-methyl propyl),3-methyl butyl, 2,2-dimethyl propyl, 2-methyl pentyl, or 3,3-dimethyl butyl groups.

If the substituents $R_1$ and/or $R_2$ indicate alkenyl, such alkenyl substituents can also be branched as well as straight-chain alkenyl grops. Straight-chain alkenyl groups are the preferred substituents, such as the allyl (2-propenyl),2-butenyl, 3butenyl, 2-pentenyl, 3pentenyl, or 4-pentenyl groups. A suitable branched alkenyl substituent is, for instance, the 2-methyl-2-propenyl group.

According to another variant of the present invention the substituents $R_1$ and $R_2$ can also be cyclo-alkyl groups and preferably cyclo-alkyl groups with 3 to 6 carbon atoms. Such cycloalkyl substituents are either directly attached to the respective nitrogen atom or by interposition of an alkylene group with 1 to 3 carbon atoms and preferably of a methylene group. Examples of such cyclo-alkyl substituents are the cyclopropyl, cyclobutyl, cyclopentyl, and cyclohexyl groups. If these cyclo-alkyl groups are attached to the respective nitrogen atoms by means of an alkylene group, the preferred intermediate alkylene group is the methylene group.

As already mentioned above, the substituents $R_1$ and $R_2$ can indicate the same or different substituents. The preferred compounds are those in which the substituents $R_1$ and $R_2$ are the same groups In so far as, according to a preferred embodiment of the present invention, the substituents $R_3$ and $R_4$ are alkyl, and more particularly straight-chain alkyl, the statements made hereinabove with respect to the substituents $R_1$ and $R_2$ apply accordingly to the substituents $R_3$ and $R_4$. Preferably each of the substituents $R_3$ and $R_4$ contains 1 to 7 carbon atoms and more particularly 1 to 4 carbon atoms.

In principle the substituents $R_3$ and $R_4$ may indicate the same or different groups. Preferred compounds according to the present invention are compounds in which the substituents $R_3$ and $R_4$ indicate the same groups.

According to a special embodiment of the present invention in which the substituent $R_3$ is the same as the substituent $R_4$, said substituents $R_3$ and $R_4$ jointly may form an alkylene chain of the Formula $—(CH_2)_n—$. In this case, the preferred values for n are between 3 and 6 and more particularly between 3 and 5.

A subgroup according to the compounds of the above given Formula I is characterized by the feature that the substituents $Z_1$ and $Z_2$ together form an oxygen group.

Said sub-group of compounds represents valuable intermediate products for the preparation of pharmacologically highly effective diaza bicyclo-(3,3,1)-nonane compounds.

Said sub-group comprises compounds of Formula I in which both substituents $R_1$ and $R_2$ indicate hydrogen. Especially selected representatives of this group of compounds are 2,4,6,8-tetra-oxo-3,7-diaza bicyclo-(3,3,1)-nonane compounds of the following Formula II in which the substituent $R_5$ is hydrogen:

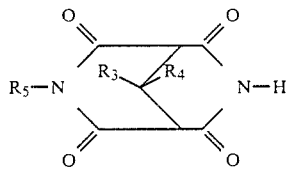

II

Furthermore, this sub-group of compounds comprises compounds of Formula I, in which only one of the substituents $R_1$ and $R_2$ is hydrogen. Representatives of this group of compounds are 2,4,6,8-tetra-oxo 3,7-diaza bicyclo-(3,3,1)-nonane compounds of Formula II in which the substituent $R_5$ indicates the same group as given for the substituent $R_1$, or such nonane compounds of the following Formula Va

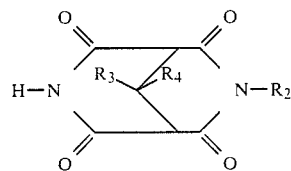

Va where $R_2$ is as previously defined, excluding hydrogen.

Compounds of Formula I in which both substituents $R_1$ and $R_2$ are not hydrogen, are also included in said sub-group of compounds. Such compounds correspond to the following Formula Vb

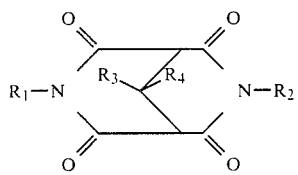

Vb

Other compounds corresponding to the following Formula Vc

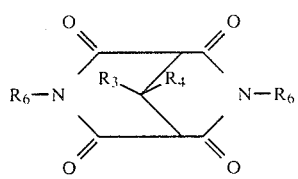

Vc in which the substituents $R_6$ correspond either to the substituent $R_1$ or to the substituent $R_2$, are comprised also be the aforesaid sub-group of compounds. Compounds of the type of Formula Vc are designated as symmetrically substituted compounds, because the same substituent is attached to both nitrogen atoms.

The second subgroup of compounds of Formula I is characterized by the feature that each of the substituents $Z_1$ and $Z_2$ indicates hydrogen.

This sub-group of compounds comprises compounds of the following Formula VIa

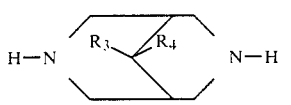

VIa

In said Formula both substituents $R_1$ and $R_2$ have already been denoted as hydrogen.

Said sub-group of compounds also comprises compounds of the following Formulas VIb or VIc in which only one of the substituents $R_1$ or $R_2$ is hydrogen.

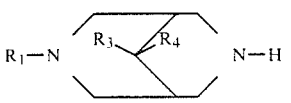

VIb

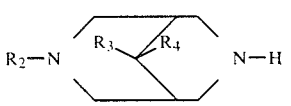

VIc

Said compounds of Formula VIa, VIb, and VIc represent also useful intermediate products for the preparation of pharmacologically especially effective diaza bicyclo-(3,3,1)-nonane compounds according to the present invention.

Furthermore, the present invention comprises also compounds in which the substituents $Z_1$ and $Z_2$ indicate hydrogen while the substituents $R_1$ and $R_2$ do not indicate hydrogen, but rather one or the other of the substituents mentioned hereinabove. These compounds correspond to the Formula VIIa

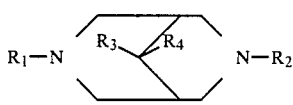

VIIa or to the Formula VIIb

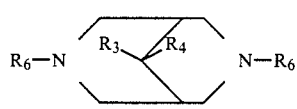

(VIIb)

The compounds of Formula VIIb are symmetrically substituted whereby the substituents $R_6$ correspond either to the substituent $R_1$ or to the substituent $R_2$ as given for the compounds of Formula I hereinabove. The compounds of Formulas VIIa and VIIb possess valuable pharmacological properties.

Especially useful representatives of compounds selected from the group characterized by Formula VIIa are, for instance, 3,7-diaza bicyclo-(3,3,1)-nonane compounds which are substituted by the following substituents:

N-Isopropyl-N'-(2-methyl propyl)-9,9-pentamethylene-,
N-Isopropyl-N'-(cyclohexyl)-methyl-9,9-di-n-butyl-,
N-n-Butyl-N'-(2-methyl propyl)-9,9-dimethyl-,
N-n-Butyl-N'-(cyclohexyl)-methyl-9,9-dimethyl-,
N-n-Hexyl-N'-methyl-9,9-diethyl-,
N-(2-Methyl propyl)-N'-(3-butenyl)-9,9-di-n-propyl-,
N-n-butyl-N'-(3-butenyl)-9,9-dimethyl-.

Selected representatives of the group of compounds characterized by Formula VIIb are 3,7-diaza bicyclo-(3,3,1)-nonane compounds with the following substituents:

N,N'-Diethyl-9,9-dimethyl-,
N,N'-Di-n-propyl-9,9-diethyl-,
N,N'-Di-isopropyl-9,9-dimethyl-,
N,N'-Di-isopropyl-9,9-di-n-propyl-,
N,N'-Di-n-butyl-9,9-dimethyl-,
N,N',9,9-Tetra-n-butyl-,
N,N'-Di-n-butyl-9-methyl-9-ethyl-,
N,N'-Di-(cyclopropyl)-methyl-9,9-tetramethylene-,
N,N'-Di-n-hexyl-9,9-dimethyl-,
N,N'-Di-n-hexyl-9-ethyl-9-n-butyl-,
N,N'-Di-n-hexyl-9,9-tetramethylene-,
N,N'-Di-(cyclohexyl)-methyl-9-methyl-9-ethyl-,
N,N'-Di-(cyclohexyl)-methyl-9,9-pentamethylene-,
N,N'-Di-n-decyl-9,9-dimethyl-,
N,N'-Di-isopropyl-9-methyl-9-n-propyl-,
N,N'-Di-n-butyl-9,9-trimethylene-,
N,N'-Di-(2-propenyl)-9,9-dimethyl-,
N,N'-Di-(3-butenyl)-9,9-pentamethylene-,
N,N'-Di-(3-butenyl)-9,9-dimethyl-,
N,N'-Di-(3-butenyl)-9-methyl-9-n-propyl-.

Furthermore, the present invention is concerned with pharmaceutical compositions which contain at least one compound of the Formula VIIa or VIIb or their pharmaceutically acceptable acid addition salts.

Suitable pharmaceutically acceptable acid addition salts are, for instance, water soluble as well as water insoluble salts with inorganic or organic acids, such as, for instance, the hydrochlorides, hydrobromides, hydroiodides, sulfates, nitrates, phosphates, perchlorates, acetates, propionates, butyrates, citrates, gluconates, benzoates, salicylates, sulfosalicylates, maleinates, laurates, fumarates, succinates, tartrates, oxalates, stearates, tosylates (p-toluyl sulfonates), 2-hydroxy-3-naphthoates, 3hydroxy-2-naphthoates, mesylates (methane sulfonates), naphthalene sulfonates, and the like.

The present invention is also concerned with providing simple and effective processes of producing 3,7-diaza bicyclo-(3,3,1)-nonane compounds of the Formula I as given hereinabove. Said process is characterized by the feature that (a) in order to produce compounds of Formula II, correspondingly substituted dinitriles of Formula III

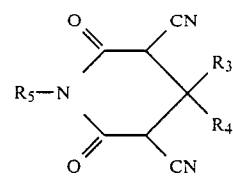

III or mononitriles of Formula IV

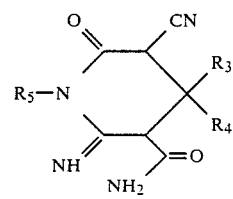

IV in which Formulas the substituent $R_5$ indicates hydrogen or the substituent $R_1$, while the substituents $R_1$, $R_3$, and $R_4$ indicate the substituents given hereinabove, are hydrolyzed under acidic conditions to the bicyclic compounds of Formula II

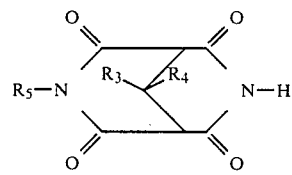

(II)

(b) In order to produce compounds of Formula V, the resulting, correspondingly substituted compounds of Formula II (b1) in which the substituent $R_5$ is hydrogen or the substituent $R_1$, are mono-alkylated with a compound of Formula $R_2X$, in which X is a reactive leaving group, to compounds of Formula Va or Vb

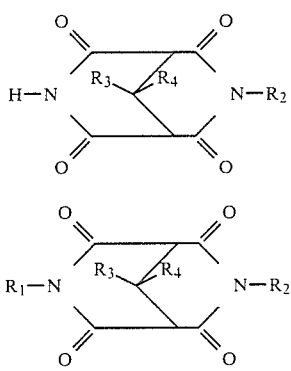

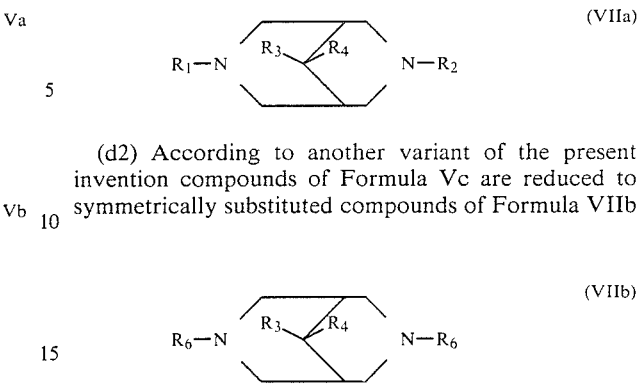

(d2) According to another variant of the present invention compounds of Formula Vc are reduced to symmetrically substituted compounds of Formula VIIb

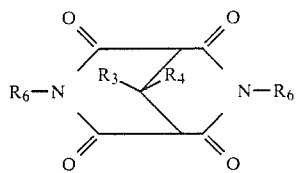

(b2) According to another embodiment of the present invention the compounds of Formula II in which the substituent $R_5$ is hydrogen are dialkylated with a compound of Formula $R_6X$ in which X is a reactive leaving group, to yield symmetrically substituted compounds of Formula Vc.

(Vc)

in which the substituents $R_6$ correspond either to the substituent $R_1$ or to the substituent $R_2$ as given hereinabove.

(b3) According to another embodiment of the alkylating process step (b) of the present invention, the compounds of Formula II in which the substituent $R_5$ is hydrogen, are successively monoalkylated with compounds of the Formulas $R_1X$ and with compounds of the Formula $R_2X$ to yield the dialkylated compounds of Formula Vb as given hereinabove.

(c) In order to produce compounds of Formula VI, the resulting, correspondingly substituted compounds of Formulas II or Va are reduced to compounds of Formulas VIa, VIb, or VIc

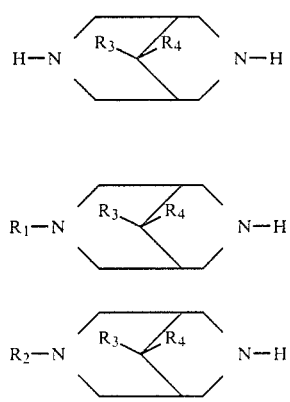

(d) Compounds of Formula VII are produced (d1) by reducing the resulting, correspondingly substituted compounds of Formula Vb to compounds of Formula VIIa (d3) By proceeding according to step (d3) compounds of Formula VIa are dialkylated by reaction with compounds of Formula $R_6X$ to yield symmetrically substituted compounds of the above given Formula VIIb.

(d4) Or according to step d4 compounds of Formula VIa are successively mono-alkylated by reaction with compounds of Formula $R_1X$ and with compounds of Formula $R_2X$ to yield compounds of Formula VIIa.

(d5) According to step d5 compounds of Formula VIb or, respectively, VIc are mono-alkylated by reaction with compounds of the Formulas $R_1X$ or, respectively, $R_2X$ to compounds of Formula VIIa.

(d6) According to step d6 compounds of Formula VIb are mono-alkylated by reaction with compounds of Formula $R_1X$, while compounds of Formula VIc are mono-alkylated with compounds of Formula $R_2X$ so as to yield symmetrically substituted compounds of Formula VIIb.

DETAILED DESCRIPTION OF PREFERRED EMBODIMENTS

In all these reaction steps the substituent X indicates a group or atom which is capable to be substituted by the nitrogen atom of the starting materials of Formulas V or VI so as to attach the group $R_1$ or the group $R_2$ to the compound of Formulas V or VI, whereby the substituent X acts as a so-called "leaving group".

The preferred sequence of reaction steps for producing the final products of Formula VIIa are the steps a, b1, or, respectively, b3, and d1. The final products of Formula VIIb are preferably produced by following the reaction steps a, b2, and d2. The intermediate products obtained by carrying out said intermediate reaction steps represent especially valuable and preferred intermediate products according to the present invention.

The 2,4,6,8-tetra-oxo-3,7-diaza bicyclo-(3,3,1)-nonane compounds of Formula II can also be prepared in an analogous manner as described in J. Am. Chem. Soc. vol. 80, page 3915 (1958) by reacting the dinitriles of Formula III

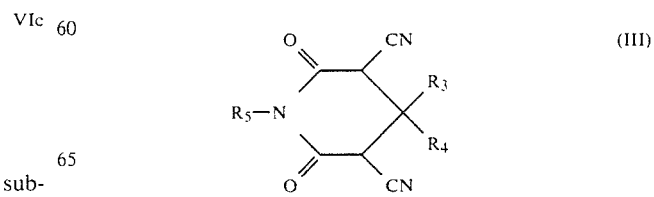

or the mononitriles of Formula IV

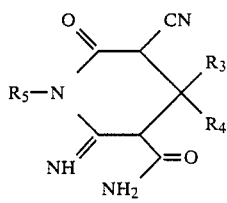

with mixtures of acid and water of a high acid content, for instance, with highly concentrated sulfuric acid or phosphoric acid. The dinitriles of Formula III are known from the literature or they can be synthetically produced in an analogous manner in accordance with known processes by condensing alkylidene acetic acid esters with cyano acetic acid amides as described in *Org. Syn.* vol. 39, page 52, or by reacting cyano acetic acid esters with ketones in ammoniacal alcohol solution in accordance with the process described in Org. Syn. vol. 36, page 28.

The mononitriles of Formula IV which are partly known from the literature, are obtained by condensation of the respective ketones with cyano acetamide in an alkaline medium as described in J. Chem. Soc. vol. 99, page 422 (1911).

The reduction of the 2,4,6,8-tetra-oxo-3,7-diaza bicyclo-(3,3,1)-nonane compounds of Formula II or, respectively, that of their N-mono-alkyl derivatives of Formula Va or, respectively, of their N,N'-dialkylation product of Formulas Vb or Vc can also be carried out in a known manner, for instance, as described in J. Am. Chem. Soc. vol. 78, page 2582 (1956) or in Israel. J. Chem. vol. 4, page 39 (1966). Complex metal hydrides such as, for instance, lithium aluminum hydride or sodium boron hydride in the presence of Lewis acids have proved to be especially advantageous reducing agents for the reduction of the oxo groups.

Preferably lithium aluminum hydride is used in a mixture of 70 parts of tetrahydrofurane and 30 parts of toluene. In contrast to the above mentioned methods or to the procedure described in *Europ. J. Med. Chem.*, vol. 12, page 301 (1977) there is achieved complete reaction in said solvent mixture already after a relatively short reaction time of about 2 hours to 4 hours. If access and action of the reducing agent are being hindered for steric reasons, for instance, when reducing N-isopropyl substituted starting compounds, more prolonged reaction times are required. It has proved to be of advantage to use an excess of the reducing agent amounting to 200% to 400% thereof.

If the tetra-oxo compounds are substituted by unsaturated groups $R_1$ and/or $R_2$, for instance, by alkene or alkine groups, sodium bis-(2-methoxy ethoxy) dihydro aluminate is used as the preferred reducing agent.

The alkylation of the tetra-oxo compounds of Formulas II or Va or that of the diaza bicyclo-(3,3,1)-nonane compounds of Formulas VIa, VIb, or VIc obtained by reduction of the tetra-oxo compounds is carried out under basic conditions, for instance, with sodium hydride in dimethyl formamide, with alkali metal carbonate in dimethyl formamide, with sodium methylate in methanol, with sodium propylate in propanol, with sodium isopropylate in isopropanol, or with sodium amide in toluene or xylene, or in accordance with the known principle of phase transfer catalysis(*), among others. The alkylation, especially that of the tetra-oxo compounds of Formulas II, Va, or Vb in which the substituent $R_1$ is hydrogen, is most advantageously effected with sodium hydride or an alkali metal carbonate is dimethyl formamide at increased temperature.

(*)=as described in *Synthesis* 1973, page 441 or *Angew. Chem., Int.Ed-.Engl.* vol. 13, page 70 (1974).

The starting materials used in the above described processes are preferably employed in stoichiometric amounts. For the alkylation of the compounds of Formulas II or, respectively, VI there is preferably employed an excess of alkylating or deprotonising agent in an amount of 25% to 70%.

As alkylating agents there are used compounds of the Formulas $R_1X$, $R_2X$, or, respectively, $R_6X$ in which the substituent X indicates a reactive "leaving" group, as it is known. More particularly the most useful alkylating agents are the corresponding alkyl halogenides, alkyl tosylates, alkyl brosylates, or alkyl mesylates. The most preferred alkylating agents are the alkyl halogenides and especially the alkyl chlorides or bromides. It is also possible to produce the alkylating agent in situ from the corresponding alcohols, for instance, according to the method of Mitsunobu, as described in *Synthesis* 1981 page 1. When proceeding according to said method, it is not necessary to add a deprotonising agent.

The reactions described hereinabove can be carried out at atmospheric pressue or also at increased pressure. Working at atmospheric pressure is the preferred procedure.

The reactions take place preferably in an inert organic solvent or in a mixture of such a solvent with water. Suitable inert organic solvents are, for instance, ethers, such as diethyl ether, dioxane, or tetrahydrofurane, halogenated hydrocarbons, such as methylene dichloride, or carbon tetrachloride, dimethyl formamide, or acetone.

The reaction temperatures at which the aforesaid processes are carried out, can vary within a range between about 20° C. and about 200° C. and preferably between 40° C. and 150° C.

Separation of mono- and di-alkylation products which might become necessary, can be effected in a manner known per se, for instance, by alkaline extraction or by chromatographic separation.

The above disclosed processes permit the preparation of compounds with the most varied pattern of substitution. Thus it is possible to achieve symmetric or asymmetric substitution in 9-position of the resulting diaza bicyclo-(3,3,1)-nonane compounds, more particularly by selecting the desired substituents $R_3$ and $R_4$ in the starting materials of Formulas III and IV. On the other hand it is also readily possible to produce N,N'-symmetrically or N,N'-asymmetrically substituted diaza bicyclo-3,3,1)-nonane compounds of Formulas II, Va, VIa, VIb, or VIc by selecting the respective alkylating agents of Formulas $R_1X$ or $R_2X$.

If the substituent $R_1$ or, respectively, the substituent $R_5$ and $R_2$ and also the substituents $R_3$ and $R_4$ are different from each other, there is obtained a mixture of stereoisomers in the various process steps. There stereoisomers can readily be separated from each other by known methods, for instance, by fractional precipitation of suitable salts of the compounds, by fractional column chromatography, or by fractional separation by adjusting the aqueous solution to varying pH-values. If the substituents $R_3$ and $R_4$ are different from each other, separation is preferably carried out with the tetra-oxo compounds of Formulas II, Va, or Vb or with the diaza bicyclo-(3,3,1)-nonane compounds of Formulas VIb or VIc obtained from the compounds of Formulas II, Va by reduction.

The acid addition salts obtainable according to the present invention are produced in a known manner by reacting the basic compounds of Formula I with acids which form pharmaceutically acceptable salts.

The compounds of Formulas VIIa and VIIb and their pharmaceutically acceptable acid addition salts are characterized and distinguished by interesting pharmacological properties. More particularly, they reduce oxygen consumption by the heart, affect heart rate, and normalize cardiac rhythm. The novel compounds according to the present invention thus have a noteworthy activity and a high physiological compatibility. As a result thereof, said novel compounds exhibit a satisfactory anti-arrhythmic activity in relatively small doses. On the other hand, only a very minor undesired negative influence on the contractile force of the heart has been observed. Accordingly, the novel compounds are characterized by an especially favorable relation between anti-arrhythmic activity or prolongation of the cardiac refractory period and negative inotropic side effects. Thus, they possess a very satisfactory therapeutic index. Surprisingly, they show a positive inotropic activity when administered in small doses.

The influence of the active compounds according to the present invention on myocardial oxygen consumption has been investigated in animal models and determined according to the method of Neill as described by W. A. Neill, H. H. Levine, R. J. Wagman, and P. Gorlin in *Circulation Research*, Vol. 12, page 163 (1963). The blood circulation measurements which are required for these tests, namely, systolic blood pressure and heart rate, were determined according to the design of experimental procedure as described by G. Buschmann, W. Schumacher, R. Budden, and U. G. Kuehl in *J. Cadiovasc. Pharmacol.*, Vol. 2, pages 777–795 (1980). As is evident from the following Table 1, the active compound reduces the product* of heart rate and systolic blood pressure. Thus, the tested compound reduces the consumption of oxygen to be supplied to the heart. This effect is observed in intravenous administration (i.v.) as well as on intraduodenal administration (i.d.) and is to be attributed to the action of the compound tested.
*=shown as DP in Table 1

The anti-arrhythmic activity of the active compounds according to the present invention was demonstrated on the intact experimental animal by means of experimentally produced disturbances of the cardiac rhythm. When administering aconitine to rats by continuous intravenous infusion, there are observed in the electrocardiogram considerable disturbances in the heartbeat, such as, for instance, ventricular extrasystoles. The tested animals were male Wistar rats of the weight class between 250 g. and 350 g. The influence of an active compound according to the present invention upon such rats after an aconitine infusion was determined according to the method of Raschak as described by M. Raschak in Arzneim. Forsch. vol. 25, No.4, pages 639–641 (1975). The results of these tests are given hereinafter in Table 2. Said Table 2 shows the difference in time, in %, at which ventricular extrasystoles were observed between a test with administration of the active compound and a control test with a control solution.

The active compound was administered intravenously in the form of an isotonic sodium chloride solution, i.e. the vehicle, in a dose of 6.0 μmole/kg. The dose administered is one twentieth of the lethal dose ($LD_{50}$) as determined on mice. (The $LD_{50}$ on peroral administration to mice of the tested compound amounts to 1038 μmole/kg.) The control test was carried out by intravenous administration of the vehicle, i.e. of an isotonic sodium chloride solution. After intravenous administration of the active compound to be tested and of the control solution, the aconitine solution was administered by infusion in an amount which was constant per time unit. The period of time was measured within which ventricular extrasystoles (ES) were observed. Said period of time, in minutes, is given in Table 2 as well as the difference in the period of time observed on administering the test compound and the control solution.

One of the active compounds tested is the compound of Example 3, No. 302, i.e., N,N-di-n-butyl-9,9-dimethyl-3,7-diaza bicyclo-(3,3,1)-nonane as described hereinafter. There are also given the results obtained by testing an equitoxic amount of the drug known under the trademark "Lidocain", i.e., 2-(diethylamino)-N-(2,6-dimethyl phenyl)-acetamide. Said compound is a known anti-arrhythmic agent which is used in human therapy and has proved to be highly effective.

TABLE 1

| | Effect upon heart rate (FRQ), systolic blood pressure ($P_s$) and the double product (DP) determined on anesthetized rate | | | | |
|---|---|---|---|---|---|
| Test compound of Formula I | Dose [μmole/kg.] | FRQ [1/min.]** | $P_s$ [mm.Hg] | DP [mm.Hg/min. × 1000] | Change DP [%] |
| Initial values | 0 | 372 | 104 | 39 | — |
| Example 3, No. 302ˣ | 13.5 i.v. | 174 | 147 | 25 | −36 |
| Initial values | 0 | 406 | 101 | 41 | — |
| Example 3, No. 302ˣ | 100 i.d. | 238 | 125 | 30 | −27 |

ˣ=administered as ditartrate
**[1/min.] means "heart beats per minute"

TABLE 2

| | Anti-arrhythmic activity determined by the aconitine test in rats | | |
|---|---|---|---|
| Test compound | Dose [μmole/kg.] | Time to occurrence of ES [min.] | Change [%] |
| Control test with vehicle | 0 | 6.7 | — |
| Example 3, No. 302 administered as di-tartrate | 6.0 | 8.2 | +23 |
| Control test with vehicle | 0 | 6.3 | — |
| Lidocain | 10.0 | 6.6 | +5 |

Furthermore the anti-arrhythmic activity of the novel active compound can be demonstrated and proved experimentally by measuring the functional refractory period of the left atrium cordis of female albino Pirbright-white guinea pigs of the weight class between 300 g. and 400 g. by means of paired electrical stimulation in accordance with the method of Govier as described in *J. Pharmacol. Exp. Ther.*, vol. 148, No. 1, pages 100–105 (1965). All anti-arrhythmic drugs which at present are used in therapy and which differ in their chemical structure are distinguished by being able to prolong the functional refractory period. In addition thereto said method permits to detect the effects of compounds on the contractile force of the myocardium. Therefore, there are given in Table 3, as the functional refractory period FRP 125% the values for those concentrations in μmole/l. which cause a prolongation of the functional refractory period to 125% 18 minutes after administration of the compound to be tested, or, respectively, as contractile force F 75% the corresponding concentrations which cause a reduction of the contractile force to 75% of the initial value. Furthermore, there is listed in Table 3 the quotient F 75%/FRP 125%, i.e. the quotient of the dose causing a decrease of the contractile force by the dose causing prolongation of the refractory period. Said quotient supplies information regarding the therapeutic index of the anti-arrhythmic action of a compound on the isolated organ. See. P. Greef in *Verhandlung der Deutschen Gesellschaft fuer Kreislaufforschung* vol. 35, pages 88–97 (1969).

The direct effect of the active compound on the heart rate (FPQ) was tested on the spontaneously beating, isolated right atrium cordis of female albino Pirbright-white guinea pigs (GP) of the weight class between 300 g. and 400 g. In Table 3 there is given, as FPQ 75%, the concentration in μmole/l. by which a decrease of the heart rate to 75% of the initial value is achieved 20 minutes after administration of the compound to be tested.

It follows from Table 3 that the novel active compound tested does not exhibit any noteworthy undesirable negative inotropic effects but that it displays an anti-arrhythmic and the heart rate reducing activity already at a very low concentration.

TABLE 3

Effect on the heart rate (FRQ) of the spontaneously beating right atrium cordis of guinea pigs as well as on the contractile force (F) and on the functional refractory period (FRP) of the electrically stimulated left atrium cordis of guinea pigs

| Test compound of Formula I | Effective concentration in (μmole/l.) | | | Quotient: F 75% / FRP 125% |
|---|---|---|---|---|
| | FRQ 75% | F 75% | FRP 125% | |
| Example 3 No. 302 administered as di-tartrate | 3 | 104 | 1 | 104 |
| Comparative compound administered as di-tartrate | about 215 | about 215 | 122 | about 2 |

The results obtained in comparative tests which were carried out with the known compound N,N',9,9-tetramethyl diaza bicyclo-(3,3,1)-nonane are also given in Table 3. Said comparative compound is very closely related in its structure to the compounds according to the present invention such as the N,N'-di-n-butyl-9,9-dimethyl-3,7-diaza bicyclo-(3,3,1)-nonane compound of Example 3, No. 302. The comparative tests clearly show the outstanding superior therapeutic index of the compounds according to the present invention in contrast to the known compounds, although said known compounds per se exhibit a therapeutic index of action which is superior over that of recognized known agents, such as, for instance, "LIDOCAIN", as follows from the expert opinion given in Table 1 of published German Patent Application No. 24 28 792.

The superior activity of the compounds according to the present invention is characterized by the combination of the following effects: The reduction of oxygen consumption by the heart, the normalization of the cardiac rhythm, a favorable influence on the heart rate, and a positive inotropic effect.

This profile of pharmacological activity renders possible the use of the new compounds in the treatment of the ischemic heart disease, of life threatening arrhythmias, and of heart failure.

The compounds according to the present invention produce the above mentioned pharmacological effects within a dosage range between about 0.1 mg./kg. and about 10 mg./kg. They can be administered enterally or parenterally.

The present invention is also concerned with a process of producing novel and valuable pharmaceutical compositions which contain at least one compound of Formulas VIIa or VIIb or their pharmaceutically useful and acceptable acid addition salts. Said process comprises mixing said active compounds with suitable inert pharmaceutically acceptable excipients and converting the resulting mixture in a known manner into the desired galenic preparations. Suitable galenic preparations may be, for instance, tablets, dragees, capsules, powders, granules, aqueous or oily suspensions, emulsions, syrups, or solutions for oral administration, suppositories for rectal application, or sterile injectable suspensions or solutions for parenteral administration.

The following examples serve to illustrate the present invention without, however, limiting the same thereto. They describe more in detail the process of producing the novel compounds of Formula I and the preparation of pharmaceutical compositions containing active compounds of said Formula.

EXAMPLE 1

General description of the procedure to be followed in order to effect cyclization so as to produce 2,4,6,8-tetraoxo-3,7-diaza bicyclo-(3,3,1)-nonane compounds of Formula II:

20 g. of the dinitrile of Formula III which was prepared in an analogous manner according to the process described in Org. Syn. vol. 39, page 52, or, respectively, 20 g. of the mononitrile of Formula IV which was prepared in an analogous manner according to the process described in J. Chem. Soc. vol. 99, page 422 (1911), are heated in about 100 ml. of an acid of the composition and concentration as given hereinafter in Tables 4a and 4b, between about 120° C. and about 140° C., while stirring, until they are completely dissolved. After about 10 minutes to about 15 minutes the entire reaction mixture is poured into ice water. The precipitated tetraoxo compound of Formula II is filtered off by suction, if required, is recrystallized, preferably from ethanol, and is dried. By proceeding in this manner, there are obtained the compounds listed in Tables 4a and 4b.

TABLE 4a

Production of tetra-oxo compounds of Formula II in which the substituent $R_5$ is hydrogen

| Compound No. | $R^3$ | $R^4$ | Acid [vol. %] | Melting point [°C.] |
|---|---|---|---|---|
| 101 x | $CH_3$ | $CH_3$ | 60% $H_2SO_4$ | above 350 |
| 102 | $C_2H_5$ | $C_2H_5$ | 60% $H_2SO_4$ | 230 |
| 103 | n-$C_3H_7$ | n-$C_3H_7$ | 60% $H_2SO_4$ | 190 |
| 104 | n-$C_4H_9$ | n-$C_4H_9$ | 65% $H_2SO_4$ | 195–199 |
| 105 | —$(CH_2)_3$— | | 60% $H_2SO_4$ | above 350 |
| 106 x | —$(CH_2)_4$— | | 60% $H_2SO_4$ | above 350 |
| 107 x | —$(CH_2)_5$— | | 60% $H_2SO_4$ | 310 |
| 108 x | $CH_3$ | $C_2H_5$ | $^+H_2SO_4/H_3PO_4$ 1:1 | 324–26 |
| 109 x | $CH_3$ | n-$C_3H_7$ | $^+H_2SO_4/H_3PO_4$ 1:1 | 275 |
| 110 | $C_2H_5$ | n-$C_4H_9$ | 70% $H_2SO_4$ | 140 | x Compounds not covered by the present invention.
$^+$concentrated $H_2SO_4$ and $H_3PO_4$.

TABLE 4b

Production of tetra-oxo compounds of Formula II in which the substituent $R_5$ corresponds to the substituent $R_1$

| Compound No. | $R_1$ | $R_3$ | $R_4$ | Acid [vol. %] | Melting point [°C.] |
|---|---|---|---|---|---|
| 150 | n-$C_4H_9$ | $CH_3$ | $CH_3$$^+$ | $H_2SO_4/H_3PO_4$ 1:1 | 175–178 |
| 151 | —$CH_2$—$CH(CH_3)_2$ | n-$C_3H_7$ | n-$C_3H_7$$^+$ | $H_2SO_4/H_3PO_4$ 1:1 | 149–153 |
| 152 | —$CH_2$—⟨⟩ | n-$C_4H_9$ | n-$C_4H_9$ | 60% $H_2SO_4$ | 140 |
| 153 | n-$C_6H_{13}$ | $C_2H_5$ | $C_2H_5$$^+$ | $H_2SO_4/H_3PO_4$ 1:1 | oil |
| 154 | —$CH_2$—$CH(CH_3)_2$ | —$(CH_2)_5$—$^+$ | | $H_2SO_4/H_3PO_4$ 1:1 | 182 |

$^+$concentrated $H_2SO_4$ and $H_3PO_4$

EXAMPLE 2

General description of the procedure to be followed in order to effect alkylation of the tetra-oxo compounds of Formula II

Variant 2a

Di-alkylation of the tetra-oxo compounds of Formula II in which the substituent $R_5$ is hydrogen, by means of alkylating agents of Formula $R_6X$ in order to produce compounds of Formula Vc.

0.1 mole of the tetra-oxo compound of Formula II as obtained according to Example 1, is weighed into a preheated three-necked flask. 200 ml. of absolute dimethyl formamide are added thereto. The mixture is heated to a temperature between about 60° C. and about 70° C. Thereupon 0.25 mole of sodium hydride, calculated as 100% NaH, are added portion by portion to said mixture which is then boiled under reflux for about 1 hour. After cooling the reaction solution, there are added drop by drop, but relatively fast, 0.3 mole of the respective alkylating agent dissolved in 50 ml. of absolute dimethyl formamide. The resulting alkylation mixture is then boiled under reflux for 3 more hours. Thereafter most of the solvent is distilled off in a vacuum. Methylene chloride is added to the residue and the mixture is washed with a 20% sodium hydroxide solution. The aqueous phase is again extracted with methylene chloride. The organic solvent phases are combined, washed several times with water, and dried over magnesium sulfate. After distilling off the solvent, the remaining residue is recrystallized from a mixture of ether and hexane.

Alternatively the alkylation is carried out with the addition of an alkali metal carbonate as basic agent instead of sodium hydride, as it is described hereinafter:

0.1 mole of the tetra-oxo compound of Formula II, obtained according to Example 1 is weighed into a preheated three-necked flask. 0.25 mole of an alkali metal carbonate and 200 ml. of absolute dimethyl formamide are added thereto. The mixture is heated to 120° C. for one hour. After cooling the resulting reaction solution, there are added drop by drop, but rather rapidly, 0.3 mole of the alkylating agent dissolved in 50 ml. of absolute dimethyl formamide. The resulting reaction mixture is then boiled under reflux until complete reaction has taken place. After working up the reaction mixture as described hereinabove, the remaining residue is recrystallized from a mixture of ether and hexane.

Some of the compounds obtained according to the above described procedure are listed and characterized in Table 5a. "A" in the column "Base" of said Table 5a indicates sodium hydride while "C" indicates an alkali metal carbonate.

Variant 2b

General description of the procedure to be followed in order to effect mono-alkylation of the tetra-oxo compounds of Formula II in which the substituent $R_5$ corresponds to the substituent $R_1$, by means of alkylating agents of Formula $R_2X$ in order to produce compounds of Formula Vb.

The procedure is the same as described hereinabove in Example 2a whereby, however, in each case half the amount of sodium hydride or, respectively, of an alkali metal carbonate as well as of the alkylating agent is used for carrying out the reaction.

By proceeding as described hereinabove in Example 2b there are obtained the compounds listed in Table 5b.

TABLE 5a

Di-alkylation of the tetra-oxo compounds of Formula II in which the substituent $R_5$ is hydrogen, by means of an alkylating agent of Formula $R_6X$ in order to produce compounds of Formula Vc

| Compound No. | $R_1$ | $R_2$ | $R_3$ | $R_4$ | X | Base | Melting point [°C.] |
|---|---|---|---|---|---|---|---|
| 201 | $C_2H_5$ | $C_2H_5$ | $CH_3$ | $CH_3$ | Br | A | 152–153 |
| 202 | n-$C_4H_9$ | n-$C_4H_9$ | $CH_3$ | $CH_3$ | Br | C | 97 |
| 203 | n-$C_6H_{13}$ | n-$C_6H_{13}$ | $CH_3$ | $CH_3$ | Br | A | 68–69 |
| 204 | $CH_2=CH-CH_2-CH_2-$ | $CH_2=CH-CH_2-CH_2-$ | $CH_3$ | $CH_3$ | Br | C | 91 |
| 205 | i-$C_3H_7$ | i-$C_3H_7$ | $CH_3$ | $CH_3$ | Br | A | 99–101 |
| 206 | n-$C_{10}H_{21}$ | n-$C_{10}H_{21}$ | $CH_3$ | $CH_3$ | Br | A | 63 |
| 207 | n-$C_3H_7$ | n-$C_3H_7$ | $C_2H_5$ | $C_2H_5$ | Cl | A | 94 |
| 208 | i-$C_3H_7$ | i-$C_3H_7$ | n-$C_3H_7$ | n-$C_3H_7$ | Br | A | 145–147 |
| 209 | $CH_3$ | $CH_3$ | n-$C_4H_9$ | n-$C_4H_9$ | J | A | 135–137 |
| 210 | n-$C_4H_9$ | n-$C_4H_9$ | n-$C_4H_9$ | n-$C_4H_9$ | Br | A | 73–75 |
| 211 | n-$C_6H_{13}$ | n-$C_6H_{13}$ | —$(CH_2)_4$— | | Br | A | 70 |
| 212 | —$CH_2$—cyclopropyl | —$CH_2$—cyclopropyl | —$(CH_2)_4$— | | Cl | A | 160–161 |
| 213 | —$CH_2$—cyclohexyl | —$CH_2$—cyclohexyl | —$(CH_2)_5$— | | Br | A | 140 |
| 214 | $CH_2=CH-CH_2-CH_2-$ | $CH_2=CH-CH_2-CH_2-$ | —$(CH_2)_5$— | | Br | C | 120 |
| 215 | n-$C_4H_9$ | n-$C_4H_9$ | $CH_3$ | $C_2H_5$ | Br | A | 82 |
| 216 | —$CH_2$—cyclohexyl | —$CH_2$—cyclohexyl | $CH_3$ | $C_2H_5$ | Br | A | 112–115 |
| 217 | i-$C_3H_7$ | i-$C_3H_7$ | $CH_3$ | n-$C_3H_7$ | Br | A | 103 |
| 218 | $CH_2=CH-CH_2-CH_2-$ | $CH_2=CH-CH_2-CH_2-$ | $CH_3$ | n-$C_3H_7$ | Br | A | 57 |
| 219 | n-$C_6H_{13}$ | n-$C_6H_{13}$ | $C_2H_5$ | n-$C_4H_9$ | Br | A | oil |
| 220 | $CH_2=CH-CH_2-CH_2-$ | $CH_2=CH-CH_2-CH_2-$ | $CH_3$ | $CH_3$ | Br | A | 128–130 |
| 221 | n-$C_4H_9$ | n-$C_4H_9$ | —$(CH_2)_3$— | | Br | A | 110 |

TABLE 5b

Mono-alkylation of the tetra-oxo compounds of Formula II in which the substituent $R_5$ corresponds to the substituent $R_1$, by means of alkylating agents of Formula $R_2X$ in order to produce compounds of Formula Vb

| Compound No. | $R_1$ | $R_2$ | $R_3=R_4$ | X | Base | Melting point [°C.] |
|---|---|---|---|---|---|---|
| 250 | n-$C_4H_9$ | —$CH_2$—$CH(CH_3)_2$ | $CH_3$ | Br | A | 80 |
| 251 | n-$C_4H_9$ | $CH_2=CH-CH_2-CH_2-$ | $CH_3$ | Br | A | 80–83 |
| 252 | n-$C_4H_9$ | —$CH_2$—cyclohexyl | $CH_3$ | Br | A | 100 |
| 253 | $CH_3$ | n-$C_6H_{13}$ | $C_2H_5$ | J | A | 93–96 |

TABLE 5b-continued

Mono-alkylation of the tetra-oxo compounds of Formula II in which the substituent $R_5$ corresponds to the substituent $R_1$, by means of alkylating agents of Formula $R_2X$ in order to produce compounds of Formula Vb

| Compound No. | $R_1$ | $R_2$ | $R_3=R_4$ | X | Base | Melting point [°C.] |
|---|---|---|---|---|---|---|
| 254 | i-$C_3H_7$ | $-CH_2-\langle\rangle$ | n-$C_4H_9$ | Br | A | 85 |
| 255 | $-CH_2-CH(CH_3)_2$ | $CH_2=CH$ $\vert$ $-CH_2-CH_2$ | n-$C_3H_7$ | Br | A | oil |
| 256 | i-$C_3H_7$ | $-CH_2-CH(CH_3)_2$ | $-(CH_2)_4-$ | Br | A | 101 |

EXAMPLE 3

General description of the procedure to be followed in order to reduce the di-alkylated tetra-oxo compounds of Formulas Vb or Vc to the 3,7-diaza bicyclo-(3,3,1)-nonane compounds of Formulas VIIa or VIIb.

0.1 mole of lithium aluminum hydride are placed with a mixture of 100 ml. of a solution of 70 ml. of absolute tetrahydrofurane and 30 ml. of absolute toluene into a preheated three-necked flask. There are slowly added thereto drop by drop 0.025 mole of the tetra-oxo compound of Formulas Vb or Vc in 100 l. of a mixture of 70 ml. of tetrahydrofurane and 30 ml. of toluene at an oil bath temperature of 80° C. The reaction mixture is kept at a temperature of 120° C. for 2 to 4 hours. Thereupon the reaction mixture is hydrolyzed under basic conditions.* The reaction mixture is then extracted with methylene chloride and the organic phase is dried over magnesium sulfate. The dried organic phase is then concentrated by evaporation. The residue is subjected to fractional distillation under reduced pressure in a destillation flask provided with a bulb-tube fractionating column. By proceeding in this manner there are obtained, for instance, the 3,7-diaza bicyclo-(3,3,1)-nonane compounds listed in Table 6a.

*=as described e.g. in *J.Org.Chem.* vol 18, page 1190 (1953).

N,N'-disubstituted tetra-oxo compounds of Formulas Vb or Vc in which the substituents at the nitrogen atoms are alkenyl groups, are reduced in an analogous manner as described hereinabove by using, as reducing agent, sodium bis-(2-methoxy ethoxy)-dihydro aluminate (sold under the trademark "Red-Al") in toluene. The reaction products obtained in this manner are listed hereinafter in Table 6b.

TABLE 6a

Reduction of the tetra-oxo compounds of Formulas Vb or, respectively, Vc to the corresponding 3,7-diaza bicyclo-(3,3,1)-nonane compounds of Formulas VIIa, or, respectively, VIIb.

| Compound No. | $R_1$ | $R_2$ | $R_3$ | $R_4$ | Boiling point [°C. at 0.1 Torr.] |
|---|---|---|---|---|---|
| 301 | $C_2H_5$ | $C_2H_5$ | $CH_3$ | $CH_3$ | 160–170 |
| 302 | n-$C_4H_9$ | n-$C_4H_9$ | $CH_3$ | $CH_3$ | 130 |
| 303 | n-$C_6H_{13}$ | n-$C_6H_{13}$ | $CH_3$ | $CH_3$ | 210–220 |
| 304 | i-$C_3H_7$ | i-$C_3H_7$ | $CH_3$ | $CH_3$ | 100–120 |
| 305 | n-$C_{10}H_{21}$ | n-$C_{10}H_{21}$ | $CH_3$ | $CH_3$ | 230 |
| 306 | n-$C_3H_7$ | n-$C_3H_7$ | $C_2H_5$ | $C_2H_5$ | 140–150 |
| 307 | i-$C_3H_7$ | i-$C_3H_7$ | n-$C_3H_7$ | n-$C_3H_7$ | 150–160 |
| 308 | n-$C_6H_{13}$ | n-$C_6H_{13}$ | $-(CH_2)_4-$ | | 250 |
| 309 | $-CH_2-\triangleleft$ | $-CH_2-\triangleleft$ | $-(CH_2)_4-$ | | 230 |
| 310 | n-$C_4H_9$ | n-$C_4H_9$ | $CH_3$ | $C_2H_5$ | 180–200 |
| 311 | n-$C_6H_{13}$ | n-$C_6H_{13}$ | $C_2H_5$ | n-$C_4H_9$ | 230 |
| 312 | n-$C_6H_{13}$ | $CH_3$ | $C_2H_5$ | $C_2H_5$ | 130 |
| 313 | $-CH_2-\langle\rangle$ | $-CH_2-\langle\rangle$ | $-(CH_2)_5-$ | | 102* |
| 314 | $-CH_2-\langle\rangle$ | $-CH_2-\langle\rangle$ | $CH_3$ | $C_2H_5$ | 36* |
| 315 | i-$C_3H_7$ | i-$C_3H_7$ | $CH_3$ | n-$C_3H_7$ | 150 |
| 316 | i-$C_3H_7$ | $-CH_2-CH(CH_3)_2$ | $-(CH_2)_5-$ | | 150 |
| 317 | i-$C_3H_7$ | $-CH_2-\langle\rangle$ | n-$C_4H_9$ | n-$C_4H_9$ | 190–200 |

TABLE 6a-continued

Reduction of the tetra-oxo compounds of Formulas Vb or, respectively, Vc to the corresponding 3,7-diaza bicyclo-(3,3,1)-nonane compounds of Formulas VIIa, or, respectively, VIIb.

| Compound No. | $R_1$ | $R_2$ | $R_3$ | $R_4$ | Boiling point [°C. at 0.1 Torr.] |
|---|---|---|---|---|---|
| 318 | n-$C_4H_9$ | $-CH_2-\langle\bigcirc\rangle$ | $CH_3$ | $CH_3$ | 160 |
| 319 | n-$C_4H_9$ | $-CH_2-CH(CH_3)_2$ | $CH_3$ | $CH_3$ | 160–170 |
| 320 | n-$C_4H_9$ | n-$C_4H_9$ | $-(CH_2)_3-$ | | 170 |
| 321 | n-$C_4H_9$ | n-$C_4H_9$ | n-$C_4H_9$ | n-$C_4H_9$ | 210 |

* = Melting point

TABLE 6b

Reduction of N—alkenyl substituted tetra-oxo compounds of Formulas Vb or, respectively, Vc to the corresponding 3,7-diaza bicyclo-(3,3,1)-nonane compounds of Formulas VIIa or, respectively, VIIb

| Compound No. | $R_1$ | $R_2$ | $R_3$ | $R_4$ | Boiling point [°C. at 0.1 Torr.] |
|---|---|---|---|---|---|
| 350 | $-CH_2-CH=CH_2$ | $-CH_2-CH=CH_2$ | $CH_3$ | $CH_3$ | 160 |
| 351 | $-CH_2-CH_2-CH=CH_2$ | $-CH_2-CH_2-CH=CH_2$ | $-(CH_2)_5-$ | | 175 |
| 352 | $-CH_2-CH_2-CH=CH_2$ | $-CH_2-CH_2-CH=CH_2$ | $CH_3$ | $CH_3$ | 150 |
| 353 | $-CH_2-CH(CH_3)_2$ | $-CH_2-CH_2-CH=CH_2$ | n-$C_3H_7$ | n-$C_3H_7$ | 170 |
| 354 | n-$C_4H_9$ | $-CH_2-CH_2-CH=CH_2$ | $CH_3$ | $CH_3$ | 165 |
| 355 | $-CH_2-CH_2-CH=CH_2$ | $-CH_2-CH_2-CH=CH_2$ | $CH_3$ | n-$C_3H_7$ | 130 |

The following Examples 4 to 6 describe pharmaceutical compositions which contain, as active agents, the pharmaceutically effective compounds according to the present invention, as well as methods of producing such pharmaceutical compositions.

EXAMPLE 4

Tablets

Composition:

| | |
|---|---|
| Active agent (compound of Example 3, No. 302 as ditartrate) | 20 parts |
| Corn starch | 30 parts |
| Lactose | 55 parts |
| Polyvinyl pyrrolidone (known under the trademark "Kollidon 25") | 5 parts |
| Magnesium stearate | 2 parts |
| Hydrogenated castor oil | 1 part |
| Total | 113 parts |

Description of production procedure:

The active compound is mixed with cornstarch and finely comminuted lactose in a suitable mixing device. The resulting mixture is thoroughly moistened with a 20% solution of polyvinyl pyrrolidone ("Kollidon 25" sold by Badische Anilin- und Soda-Fabrik (BASF)) in isopropanol. If required, further amounts of isopropanol are added. The resulting moistened granulate is passed through a 2 mm. mesh-sieve. The sieved mixture is dried on latticed screens at 40° C. and is passed through a sieve of a 1 mm. mesh width on a Frewitt machine. The resulting granulate is mixed with magnesium stearate and hydrogenated castor oil and the mixture is pressed to tablets, each tablet weighing 113 mg. and containing 20 mg. of the active compound.

EXAMPLE 5

Capsules

Composition:

| | |
|---|---|
| Active agent (compound of Example 3, No. 302 as ditartrate) | 20 parts |
| Corn starch | 20 parts |
| Lactose | 45 parts |
| Polyvinyl pyrrolidone ("Kollidon 25") | 3 parts |
| Magnesium stearate | 1.5 parts |
| Silica gel (known under the trademark "Aerosil 200") | 0.5 parts |
| Total: | 90 parts |

Description of production procedure:

The active agent is mixed with the corn starch and the finely comminuted lactose in a suitable mixing device. The resulting mixture is thoroughly moistened by means of a 20% solution of polyvinyl pyrrolidone ("Kollidon 25") in isopropanol. If required, more isopropanol is admixed. The resulting moist granulate is passed through a sieve of 1.6 mm. mesh width on a Frewitt machine. The sieved material is dried at 40° C. on a latticed screen. Thereupon the sieved and dried granulate is passed through a sieve of a mesh width of 1 mm., also of the Frewitt type. The resulting sieved granulate is then mixed with the magnesium stearate and the silica gel ("Aerosil 200" sold by the firm Degussa). Portions of 90 mg. each of the resulting mixture are then filled by means of an automatic encapsulating machine into capsules of size 4 consisting of hardened gelatin. When proceeding in this manner, each capsule contains 20 mg. of the active agent.

EXAMPLE 6

Ampoules

Composition (per ampoule):

| Active agent (compound of Example 3, No. 302, as ditartrate) | 5 mg. |
| Sodium chloride | 16 mg. |
| Water pro injectione ad | 2.0 ml. |

Description of production procedure:

The sodium chloride is dissolved in the water pro injectione. The active compound is added thereto and is dissolved therein by stirring the mixture. Sufficient water pro injectione is added to the solution to adjust the same to its final volume. The resulting solution is filtered through a membrane filter (0.25μ). 2.15 ml. of the filtered solution are then filled in each ampoule consisting of brown colored glass. The ampoules are then sealed and are steam sterilized at 121° C. for 30 minutes. 2 ml. of the solution used for injection contains 5 mg. of the active compound.

Of course, many changes and variations may be made in the process of producing the claimed compounds, in the starting materials, solvents, cyclization, alkylation, and reducing agents employed, in the methods of working up and purifying the resulting reaction products, and in the method of producing the pharmaceutical compositions containing the active agents, and the like, may be made by those skilled in the art in accordance with the principles set forth herein and in the claims annexed hereto.

What is claimed is:

1. A compound represented by the formula I

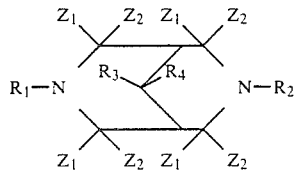

I wherein $Z_1$ and $Z_2$ each denotes hydrogen, $R_1$ and $R_2$ each denotes (A) a substituent which contains up to 12 carbon atoms and which is selected from the group consisting of alkyl, alkenyl, and alkinyl, or (B) a cycloalkyl group containing 3 to 6 carbon atoms which is attached to the nitrogen atom directly or by an alkylene group containing 1 to 3 carbon atoms, and $R_3$ and $R_4$ each denotes an alkyl group containing up to 7 carbon atoms, or both together form an alkylene chain represented by the formula $-(CH_2)_n-$, wherein n is an integer ranging between 3 and 6, such that the substituents $R_1$, $R_2$, $R_3$, and $R_4$ together contain at least 6 carbon atoms.

2. The compound according to claim 1, wherein each of said substituents $R_1$ and $R_2$ contains up to 12 carbon atoms and is selected from the group consisting of alkyl, alkenyl, and alkinyl.

3. The compound according to claim 1, wherein each of said substituents $R_1$ and $R_2$ contains up to 7 carbon atoms.

4. The compound according to claim 1, wherein at least one of said substituents $R_1$ and $R_2$ denotes a substituent selected from the group consisting of straight-chain alkyl and straight-chain alkenyl.

5. The compound of claim 1, wherein at least one of said substituents $R_1$ and $R_2$ denotes a substituent selected from the group consisting of branched alkyl and branched alkenyl.

6. The compound according to claim 1, wherein at least one of said substituents $R_1$ and $R_2$ denotes a substituent selected from the group consisting of cycloalkyl attached directly to the nitrogen atom and cycloalkyl attached to the nitrogen atom by an alkylene group containing 1 to 3 carbon atoms.

7. The compound according to claim 6, wherein at least one of said substituents $R_1$ and $R_2$ denotes a cycloalkyl substituent containing 3 to 6 carbon atoms which is attached to the nitrogen atom by a methylene group.

8. The compound according to claim 1, wherein substituents $R_1$ and $R_2$ are the same.

9. The compound according to claim 1, wherein substituents $R_3$ and $R_4$ each denotes alkyl containing up to 7 carbon atoms.

10. The compound according to claim 9, wherein substituents $R_3$ and $R_4$ each denotes alkyl containing up to 4 carbon atoms.

11. The compound according to claim 9, wherein at least one of said substituents $R_3$ and $R_4$ denotes straight-chain alkyl.

12. The compound according to claim 9, wherein substituents $R_3$ and $R_4$ are the same.

13. The compound according to claim 1, wherein substituents $R_3$ and $R_4$ together form an alkylene chain of the formula $-(CH_2)_n-$, wherein n is an integer ranging between 3 and 6.

14. The compound according to claim 13, wherein n is an integer ranging between 3 to 5.

15. The compound according to claim 1, wherein each of said substituents $R_1$ and $R_2$ are n-butyl, each of said substituents $R_3$ and $R_4$ are methyl, and each of said substituents $Z_1$ and $Z_2$ are hydrogen, said compound being N,N'-di-n-butyl-9,9-dimethyl-3,7-diaza bicyclo-(3,3,1)-nonane or its pharmaceutically acceptable acid addition salts.

16. The compound according to claim 1, wherein said substituents $R_1$, $R_2$, $R_3$, and $R_4$ together contain 8 carbon atoms.

17. The compound according to claim 16, wherein said substituents $R_1$ and $R_2$ each denote an alkenyl group.

18. The compound according to claim 1, wherein said substituents $R_1$, $R_2$, $R_3$, and $R_4$ together contain 10 carbon atoms.

19. The compound according to claim 1, wherein said substituents $R_1$, $R_2$, $R_3$, and $R_4$ together contain 12 carbon atoms.

20. The compound according to claim 19, wherein said substituents $R_3$ and $R_4$ together form an alkylene chain represented by the formula $-(CH_2)_4-$.

21. The compound according to claim 1, wherein said substituents $R_1$, $R_2$, $R_3$, and $R_4$ together contain 13 carbon atoms.

22. A pharmaceutical composition comprising (A) an amount of at least one compound selected from the group consisting of (i) a compound represented by formula I

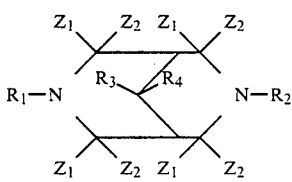

wherein
$Z_1$ and $Z_2$ each denotes hydrogen,
$R_1$ and $R_2$ each denotes (a) a substituent which contains up to 12 carbon atoms and which is selected from the group consisting of alkyl, alkenyl and alkinyl, or (b) a cycloalkyl group containing 3 to 6 carbon atoms which is attached to the nitrogen atom directly or by an alkylene group containing 1 to 3 carbon atoms, and
$R_3$ and $R_4$ each denotes an alkyl group containing up to 7 carbon atoms, or both together form an alkylene chain represented by the formula $-(CH_2)_n-$, wherein n is an integer ranging between 3 and 6,
such that the substituents $R_1$, $R_2$, $R_3$ and $R_4$ together contain at least 5 carbon atoms, and (ii) a pharmaceutically acceptable acid addition salt of said compound (i), said amount being therapeutically effective in treating cardiac arrhythmia, in treating ischemic heart disease, and/or in reducing heart rate; and (B) an inert pharmaceutically acceptable excipient.

23. A pharmaceutical composition comprising (A) an amount of at least one compound selected from the group consisting of
(1) a compound of formla VIIa

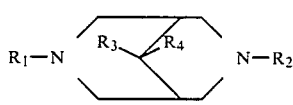

(2) a compound of formla VIIb

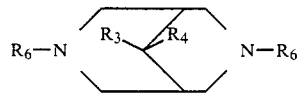

wherein
$R_1$ and $R_2$ each denotes a substituent selected from the group consisting of alkyl alkenyl, and alkinyl,
$R_3$ and $R_4$ each denotes an alkyl group, or both together form an alkylene group,
$R_6$ denotes a substituent $R_1$ or $R_2$, as previously defined, said substituents $R_1$, $R_2$, $R_3$, and $R_4$ in formula VIIa and substituents $R_6$, $R_3$ and $R_4$ in formula VIIb together containing, respectively, at least 5 carbon atoms, and
(3) a compound selected from the group consisting of the pharmaceutically acceptable acid addition salts of said compounds (1) and (2), said amount being therapeutically effective in treating cardiac arrhythmia, in treating ischemic heart diesease, and/or in reducing heart rate;
and (B) an inert pharmaceutically acceptable excipient.

24. A method for treating cardiac arrhythmias and ischemic heart disease, comprising the step of administering a therapeutically effective amount of (1) at least one compound represented by formula I

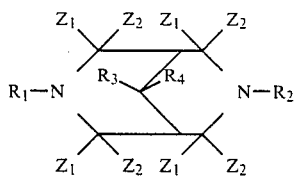

wherein
$Z_1$ and $Z_2$ each denotes hydrogen,
$R_1$ and $R_2$ each denotes (A) a substitutent which contains up to 12 carbon atoms and which is selected from the group consisting of alkyl, alkenyl, and alkinyl, or (B) a cycloalkyl group containing 3 to 6 carbon atoms which is attached to the nitrogen atom directly or by an alkylene group containing 1 to 3 carbon atoms, and
$R_3$ and $R_4$ each denotes an alkyl group containing up to 7 carbon atoms, or both together form an alkylene chain represented by the formula $-(CH_2)_n-$, wherein n is an integer ranging between 3 and 6,
such that the substituents $R_1$, $R_2$, $R_3$ and $R_4$ together contain at least 5 carbon atoms;
or (2) a pharmaceutically acceptable acid addition salt of said compound.

* * * * *